United States Patent
Pianca et al.

(10) Patent No.: US 8,792,993 B2
(45) Date of Patent: Jul. 29, 2014

(54) LEADS WITH TIP ELECTRODE FOR ELECTRICAL STIMULATION SYSTEMS AND METHODS OF MAKING AND USING

(71) Applicant: Boston Scientific Neuromodulation Corporation, Valencia, CA (US)

(72) Inventors: Anne Margaret Pianca, Santa Monica, CA (US); Joshua Dale Howard, North Hollywood, CA (US); William George Orinski, Reno, NV (US)

(73) Assignee: Boston Scientific, Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/906,776

(22) Filed: May 31, 2013

(65) Prior Publication Data

US 2013/0325091 A1    Dec. 5, 2013

Related U.S. Application Data

(60) Provisional application No. 61/654,579, filed on Jun. 1, 2012.

(51) Int. Cl.
*A61N 1/00* (2006.01)
*A61N 1/05* (2006.01)
*A61N 1/36* (2006.01)

(52) U.S. Cl.
CPC .............. *A61N 1/0534* (2013.01); *A61N 1/056* (2013.01); *A61N 1/3605* (2013.01); *A61N 1/0565* (2013.01); *A61N 1/0529* (2013.01)
USPC ......................................................... 607/116

(58) Field of Classification Search
CPC ... A61N 1/0529; A61N 1/0534; A61N 1/056; A61N 1/0565; A61N 1/3605; A61N 1/05
USPC ........................................................... 607/116
See application file for complete search history.

(56) References Cited

U.S. PATENT DOCUMENTS 4,413,636 A * 11/1983 Jasso ............................. 607/122
4,602,624 A    7/1986 Naples et al.
(Continued)

FOREIGN PATENT DOCUMENTS

| EP | 0580928 A1 | 2/1994 |
|---|---|---|
| EP | 0650694 B1 | 7/1998 |

(Continued)

OTHER PUBLICATIONS

International Application No. PCT/US2013/043588 International Search Report & Written Opinion mailed Jan. 31, 2014.

(Continued)

*Primary Examiner* — George Manuel
(74) *Attorney, Agent, or Firm* — Lowe Graham Jones PLLC; Bruce E. Black

(57) ABSTRACT

An implantable electrical stimulation lead includes a tip electrode disposed on a distal tip of the lead body. One tip electrode has a base and a separate plug attached to the base. The base defines an interior lumen closed at one end by the plug. Another tip electrode has an electrode body, a stem extending from the electrode body, and shaped retention features extending from the stem. Yet another tip electrode has an electrode body, a stem extending from the electrode body, and a flange disposed on the stem opposite the electrode body. A further tip electrode has an electrode body defining an interior lumen and a plurality of protrusions extending into the interior lumen. Another tip electrode has an electrode body and arms extending from the electrode body. The electrode body defines an interior lumen and the arms extend over an opening to the interior lumen.

20 Claims, 7 Drawing Sheets

(56) References Cited

U.S. PATENT DOCUMENTS

| | | |
|---|---|---|
| 4,630,611 A | 12/1986 | King |
| 4,744,370 A | 5/1988 | Harris |
| 4,844,099 A | 7/1989 | Skalsky et al. |
| 5,000,194 A | 3/1991 | van den Honert et al. |
| 5,097,843 A | 3/1992 | Soukup et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,391,985 B2 | 3/2013 | McDonald |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | Mcdonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |

OTHER PUBLICATIONS

U.S. Appl. No. 12/177,823, filed Jul. 22, 2008.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.
U.S. Appl. No. 13/951,057, filed Jul. 25, 2013.
U.S. Appl. No. 61/022,953, filed Jan. 23, 2008.
U.S. Appl. No. 61/316,759, filed Mar. 23, 2010.
U.S. Appl. No. 14/053,112, filed Oct. 14, 2013.

* cited by examiner

LEADS WITH TIP ELECTRODE FOR ELECTRICAL STIMULATION SYSTEMS AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/654,579 filed on Jun. 1, 2012, which is incorporated herein by reference.

FIELD

The invention is directed to the area of electrical stimulation systems and methods of making and using the systems. The present invention is also directed to electrical stimulation leads with a tip electrode designed to facilitate retention of the tip electrode on the distal end of the lead, as well as methods of making and using the leads and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

One embodiment is an implantable electrical stimulation lead including a lead body having a distal portion, a distal tip, and a proximal portion; a plurality of electrodes disposed along the distal portion of the lead body; a plurality of terminals disposed along the proximal portion of the lead; and a plurality of conductors, each conductor electrically coupling at least one of the electrodes to at least one of the terminals. The plurality of electrodes includes a tip electrode disposed on the distal tip of the lead body. The tip electrode has a base and a separate plug attached to the base. The base defines an interior lumen closed at one end by the plug. A portion of the lead body extends into the interior lumen of the base.

Another embodiment is an implantable electrical stimulation lead including a lead body having a distal portion, a distal tip, and a proximal portion; a plurality of electrodes disposed along the distal portion of the lead body; a plurality of terminals disposed along the proximal portion of the lead; and a plurality of conductors, each conductor electrically coupling at least one of the electrodes to at least one of the terminals. The plurality of electrodes includes a tip electrode disposed on the distal tip of the lead body. The tip electrode has an electrode body, a stem extending from the electrode body, and a plurality of shaped retention features extending from the stem. A portion of the lead body extends around the stem and shaped retention features. The shaped retention features facilitate retention of the tip electrode on the lead body.

Yet another embodiment is an implantable electrical stimulation lead including a lead body having a distal portion, a distal tip, and a proximal portion; a plurality of electrodes disposed along the distal portion of the lead body; a plurality of terminals disposed along the proximal portion of the lead; and a plurality of conductors, each conductor electrically coupling at least one of the electrodes to at least one of the terminals. The plurality of electrodes includes a tip electrode disposed on the distal tip of the lead body. The tip electrode has an electrode body, a stem extending from the electrode body, and a flange attached to the stem opposite the electrode body. A portion of the lead body extends around the stem and flange. The flange facilitates retention of the tip electrode on the lead body.

A further embodiment is an implantable electrical stimulation lead including a lead body having a distal portion, a distal tip, and a proximal portion; a plurality of electrodes disposed along the distal portion of the lead body; a plurality of terminals disposed along the proximal portion of the lead; and a plurality of conductors, each conductor electrically coupling at least one of the electrodes to at least one of the terminals. The plurality of electrodes includes a tip electrode disposed on the distal tip of the lead body. The tip electrode has an electrode body and the electrode body defines an interior lumen and a plurality of protrusions extending into the interior lumen. A portion of the lead body extends into the interior lumen of the electrode body. The plurality of protrusions in the interior lumen facilitates retention of the tip electrode on the lead body and hinders rotation of the tip electrode around the distal tip of the lead body.

Another embodiment is an implantable electrical stimulation lead including a lead body comprising a distal portion, a distal tip, and a proximal portion; a plurality of electrodes disposed along the distal portion of the lead body; a plurality of terminals disposed along the proximal portion of the lead; and a plurality of conductors, each conductor electrically coupling at least one of the electrodes to at least one of the terminals. The plurality of electrodes includes a tip electrode disposed on the distal tip of the lead body. The tip electrode has an electrode body and a plurality of arms extending from the electrode body. The electrode body defines an interior lumen and an opening to the interior lumen. The plurality of arms extends over the opening to the interior lumen. A portion of the lead body extends into the interior lumen of the electrode body and around the plurality of arms. The plurality of arms facilitates retention of the tip electrode on the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to electrical stimulation leads with a tip electrode designed to facilitate retention of the tip electrode on the distal end of the lead, as well as methods of making and using the leads and electrical stimulation systems.

A lead for deep brain stimulation may include stimulation electrodes, recording electrodes, or a combination of both. In at least some embodiments, the stimulation or recording electrodes of the lead can include a tip electrode and one or more ring electrodes or segmented electrodes or any combination thereof. In at least some embodiments, at least some of the stimulation electrodes, recording electrodes, or both are provided in the form of segmented electrodes that extend only partially around the circumference of the lead. In some embodiments, these segmented electrodes may be provided in sets of electrodes, with each set having electrodes radially distributed about the lead at a particular longitudinal position. In some embodiments, the segmented electrodes can be provided in any other suitable arrangement including, for example, arranging segmented electrodes in one or more helices around the circumference of the lead or arranging segmented electrodes along only one side of the lead.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation including, but not limited to, spinal cord stimulation, dorsal root ganglion stimulation, and stimulation of other nerves, muscle tissue, or organs.

Deep brain stimulation devices and leads are described in, for example, U.S. Pat. No. 7,809,446; and U.S. Patent Application Publications Nos. 2007/0150036; 2009/0187222; 2009/0276021; 2010/0076535; 2010/0268298; and 2011/0078900; and U.S. patent application Ser. Nos. 12/177,823; 61/022,953; and 61/316,759. Each of these references is incorporated herein by reference.

Figure 1:
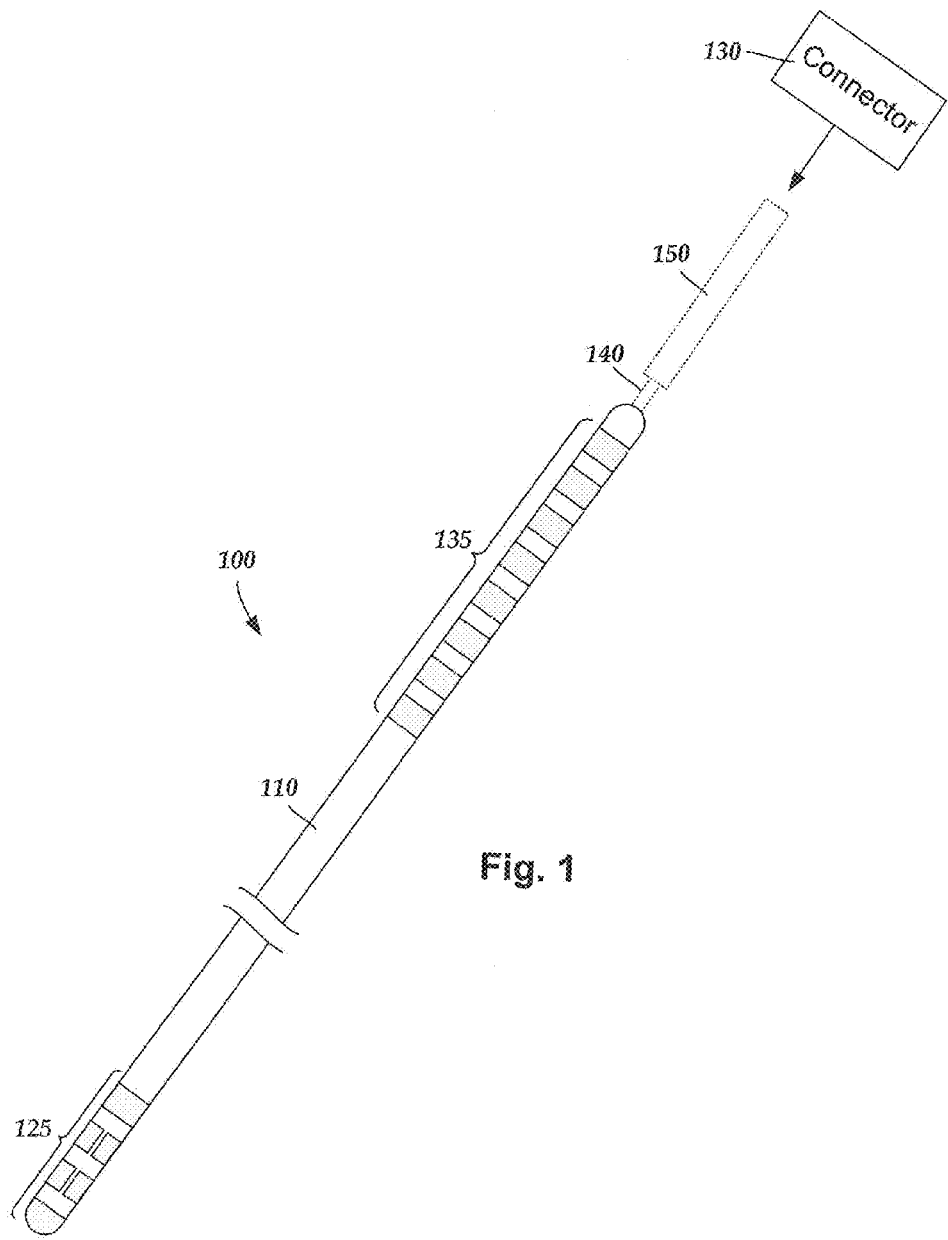
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

Figure 2:
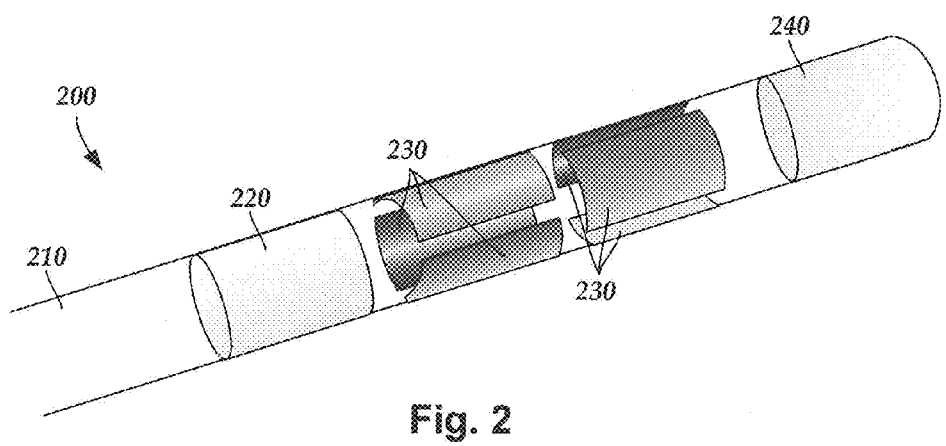
FIG. 2 is a schematic perspective view of one embodiment of a portion of a lead having a plurality of segmented electrodes and a tip electrode, according to the invention.
Figure 3:
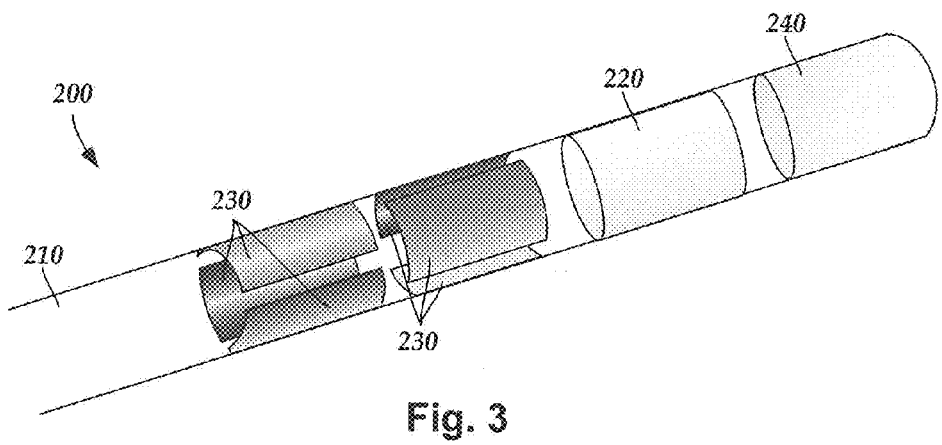
FIG. 3 is a schematic perspective view of a second embodiment of a portion of a lead having a plurality of segmented electrodes and a tip electrode, according to the invention.

FIGS. 2 and 3 illustrate embodiments of a distal portion of a lead 200 for brain stimulation. The lead 200 includes a lead body 210, one or more optional ring electrodes 220, a plurality of segmented electrodes 230, and a tip electrode 240. It will be understood that other lead embodiments can include only a tip electrode and one or more ring electrodes or only a tip electrode and one or more segmented electrodes. Other embodiments can include a tip electrode and a combination of ring and segmented electrodes in arrangements other than those illustrated in FIGS. 2 and 3.

The lead body 210 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The electrodes 220, 230, 240 may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes 220, 230, 240 can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. A stimulation electrode in the form of tip electrode 240 is disposed at the distal end of the lead. In FIG. 2, the lead 200 includes one ring electrode 220 and one tip electrode 240. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210.

In some embodiments, the ring electrode(s) 220 and tip electrode 240 are substantially cylindrical and wrap around the entire circumference of the lead body 210. The tip electrode 240 also extends over the tip of the lead. In some embodiments, the outer diameters of the ring electrode(s) 220 and tip electrode 240 are independently substantially equal to the outer diameter of the lead body 210. The length of the ring electrode(s) 220 and tip electrode 240 may independently vary according to the desired treatment and the location of the target neurons or other tissue. In some embodiments the length of one or more of the ring electrode(s) 220 and tip electrode 240 are less than or equal to the corresponding diameters of the ring electrode(s) 220 and tip electrode 240. In other embodiments, the lengths of one or more of the ring electrode(s) 220 and tip electrode are greater than the corresponding diameters of the ring electrode(s) 220 and tip electrode 240. In at least some embodiments, the surface area of the tip electrode 240 and one of the ring electrode(s) 220 may be equal of substantially equal (e.g., within 10% or 5% of each other).

Deep brain stimulation leads and other leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,295,944; and 8,391,985; and U.S. Patent Applications Publication Nos. 2010/0268298; 2011/0005069; 2011/0078900; 2011/0130817; 2011/0130818; 2011/0238129; 2011/0313500; 2012/0016378; 2012/0046710; 2012/0165911; 2012/0197375; 2012/0203316; 2012/0203320; and 2012/0203321, all of which are incorporated herein by reference.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal portion of the lead 200. The lead 200 may have any number of segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Conductor wires that attach to the tip electrode 240, ring electrode(s) 220, and segmented electrodes 230 extend along the lead body 210. These conductor wires may extend through the material of the lead 200 or along one or more lumens defined by the lead 200, or both. The conductor wires are presented at a connector (via terminals) for coupling of the electrodes 220, 230, 240 to a control unit (not shown).

When the lead 200 includes a tip electrode 240, ring electrode(s) 220 and segmented electrodes 230, the ring electrodes 220 and the segmented electrodes 230 may be arranged in any suitable configuration. The tip electrode 240 will generally be at the distal tip of any arrangement containing a tip electrode 240. For example, when the lead 200 includes a tip electrode 240, a ring electrode 220 and two sets of segmented electrodes 230, the tip electrode 240 and ring electrode 220 can flank the two sets of segmented electrodes 230 (see e.g., FIG. 2). Alternately, the tip electrode 240 and ring electrode 220 can be disposed distal to the two sets of segmented electrodes 230 (see e.g., FIG. 3). It will be understood that other configurations are possible as well (e.g., alternating ring and segmented electrodes, or the like).

Any combination of tip electrode 240, ring electrodes 220, and segmented electrodes 230 may be disposed on the lead 200. For example, the lead may include a ring electrode, two sets of segmented electrodes, each set formed of three segmented electrodes 230, and a tip electrode at the end of the lead. This configuration may simply be referred to as a 1-3-3-1 configuration as illustrated in FIG. 2. It may be useful to refer to the electrodes with this shorthand notation. FIG. 3 illustrates a lead with a 3-3-1-1 configuration. Possible configurations for a 16-electrode lead with a tip electrode include, but are not limited to, 3-3-3-3-3-1 and 1-3-3-2-3-3-1.

Markers or other indicia may be provided sot that the practitioner can determine the orientation of the segmented electrodes when implanted. Examples of suitable markers and indicia can be found in, for example, U.S. Patent Application Publications Nos. 2012/0016378 and 2012/0203321 and U.S. patent application Ser. Nos. 13/750,725 and 13/787,171, all of which are incorporated herein by reference.

Figure 4:
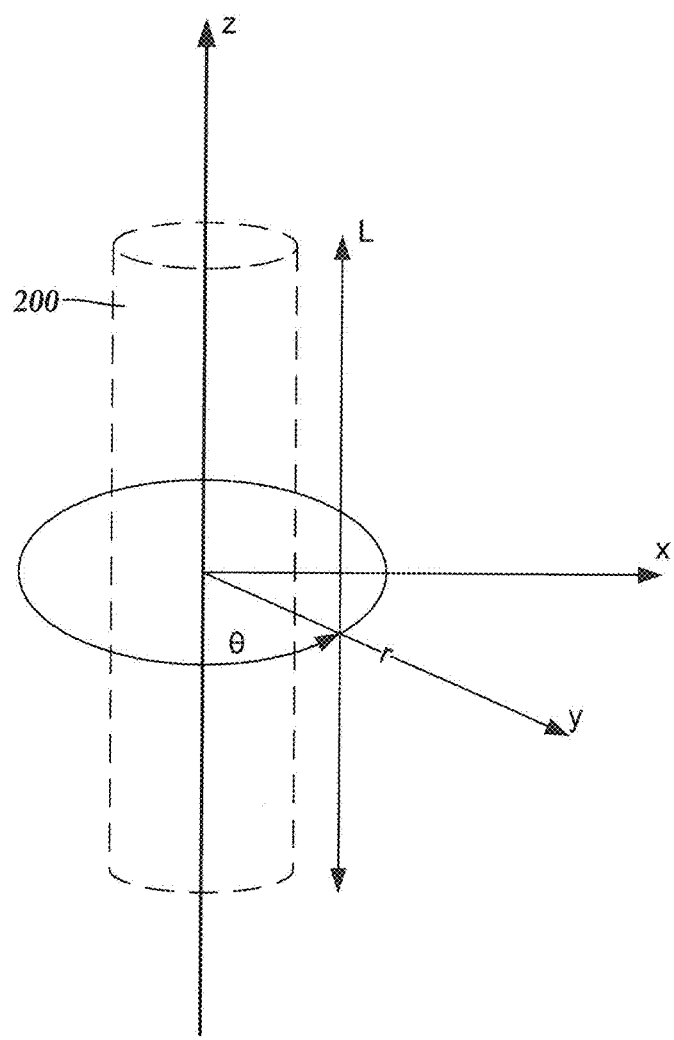
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

A tip electrode can be used in combination with one or more ring electrodes, one or more segmented electrodes, or any combination of ring and segmented electrodes. In at least some embodiments, a tip electrode may be selected to have the same, or substantially the same, surface area as one or more ring electrodes of the lead.

Figure 5:
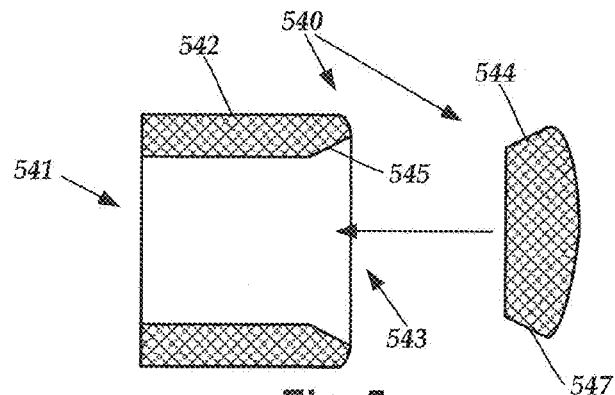
FIG. 5 is a schematic cross-sectional view of one embodiment of a two piece tip electrode, according to the invention.

A tip electrode can be designed to improve retention of the tip electrode on the lead. For example, a tip electrode may have a hollow cylindrical base and a separate plug that can be attached to the base. FIG. 5 illustrates a tip electrode 540 having a base 542 and a separate plug 544. The base 542 and plug 544 are typically formed of a suitable metal, alloy, or other conductor. The base 542 is a hollow tubular structure with an interior lumen 541 with openings at opposing ends of the tubular structure that will allow material to flow through the base. The open interior lumen 541 facilitates retention of the base on the lead. The base 542 includes a distal opening 543 that is shaped to receive the plug 544. In some embodiments, the base 542 will have sloped edges 545 at the distal opening 543 that correspond to sloped edges 547 on the plug 544 to facilitate mating of the base and plug. It will be understood that other configurations of the distal opening and corresponding surface on the plug can be used to facilitate mating of the base and plug.

Figure 6A:
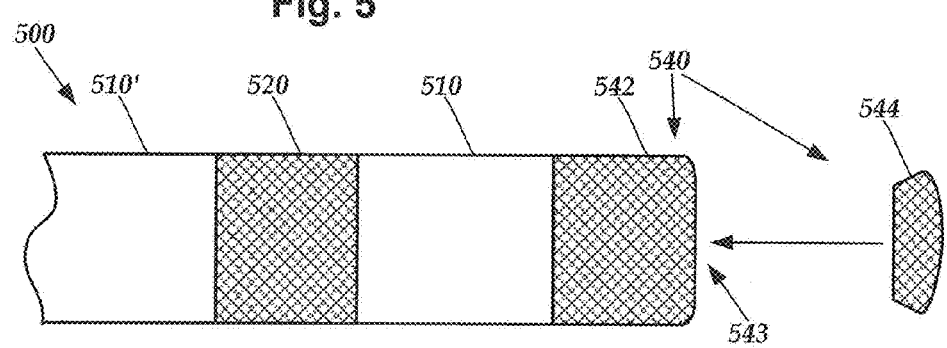
FIG. 6A is a schematic side view of an embodiment of a portion of a lead with a two-piece tip electrode prior to coupling of the two pieces together, according to the invention.
Figure 6B:
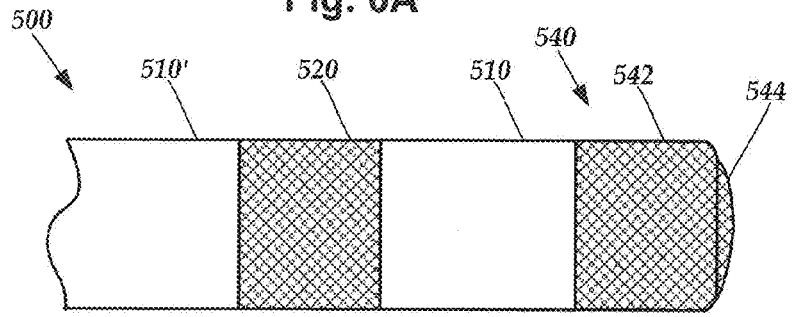
FIG. 6B is a schematic side view of the portion of the lead of FIG. 6A with the two pieces of the tip electrode coupled together, according to the invention.

FIGS. 6A and 6B illustrate a distal portion of one embodiment of a lead 500 having a tip electrode 540 with a base 542 and a separate plug 544. The lead also includes a lead body 510, 510' and one or more additional electrodes 520. In at least some embodiments the lead body 510 is formed by molding the lead body 510' between the electrodes 520 (and, at least in some embodiments, between the electrodes and the terminals at the proximal end of the lead—see, FIG. 1). The material of the lead body 510 can also be molded between the distal-most electrode 520 and the base 542 of the tip electrode 540. During the molding process, the material that will form the lead body can flow into the interior lumen 541 (see, FIG. 5) of the base 542. Any molding process can be used including, but not limited to, injection molding. The lead body 510, 510' can be formed of any material that can be molded by flowing the material around the other components and then solidify the material to form the lead body. Any suitable process can be used to solidify the material including, but not limited to, cooling the material, photocuring, heat curing, crosslinking, and the like. Examples of suitable materials can include silicone, polyurethane, polyetheretherketone, and the like. As an example, the methods for forming a lead with segmented electrodes disclosed in U.S. Patent Application Publication No. 2011/0078900, incorporated herein by reference, can be modified to include a tip electrode (by, for example, replacing the distal-most ring electrode in FIGS. 7A-7E with a tip electrode).

When the lead body 510 is formed, the lead body will extend into the interior lumen of the base 542 and facilitate retention of the tip electrode 540 on the lead 500. After the lead body 510 is formed, the plug 544 can be attached (preferably, permanently) to the base 542 by, for example, welding, soldering, adhesive (preferably, conductive adhesive), press-fit, crimping, threading on the base and plug, or any combination thereof or any other suitable fastening arrangement. Preferably, the plug 544 and base 542 are also in electrical communication with each through the fastening arrangement. In at least some embodiments, a portion of the lead body may be removed from the distal opening 543 of the base 542 to allow attachment of the plug 544 to the base.

A tip electrode conductor (not shown) is attached, welded, soldered, or otherwise electrically coupled to the tip electrode 540. The coupling of the tip electrode conductor may occur prior to forming the lead body 510. The tip electrode conductor, like other conductors in the lead, extends along the lead and is electrically coupled to one of the terminals disposed along the proximal end of the lead. In some embodiments, the tip electrode conductor is coupled to the base 542 at, for example, the surface of the interior lumen 541 or the proximal end of the base. In some embodiments, the tip electrode conductor is attached to the plug 544.

Figure 7:
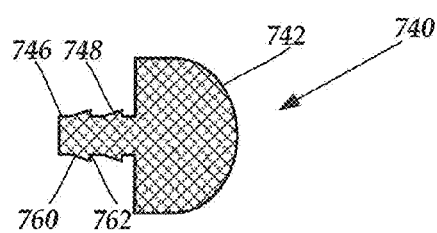
FIG. 7 is a schematic cross-sectional view of one embodiment of a tip electrode with a stem, according to the invention.

A tip electrode may include a stem with one or more features to facilitate retention of the tip electrode at the distal end of the lead. FIG. 7 illustrates in cross-section one embodiment of a tip electrode 740 having an electrode body 742 and a stem 746 with shaped retention features 748 formed on the stem. The electrode body 742 includes at least a portion of the surface that is exposed to tissue, when the lead is implanted, for providing stimulation to the tissue. When the lead body is formed, the material of the lead body forms around the stem of the tip electrode and facilitates retention of the tip electrodes within the lead body of the resulting lead. The shaped retention features 748 hinder extraction of the tip electrode from the lead body. The shaped retention features 748 on the stem typically extend away from the adjacent portions of the stem 746 to interact with material at the distal end of the lead, such as the lead body, to resist withdrawal of the tip electrode 740 from the distal end of the lead. Examples of suitable shaped retention features include, but are not limited to, one or more stepped features, sloped protrusions, flanges, teeth, protruding threads, or the like formed on the stem or a roughened surface formed on the stem. In the embodiment illustrated in FIG. 7, the shaped retention features have a sloping surface 760 on one side and a stepped surface 762 on the other side to resist withdrawal from the distal end of the lead.

A tip electrode conductor (not shown) is attached, welded, soldered, or otherwise electrically coupled to the tip electrode 740. In some embodiments, the tip electrode conductor is coupled to the stem 746. For example, the tip electrode conductor could be coupled to the side of the stem 746 or the proximal end of the stem. In other embodiments, the tip electrode conductor can be attached to the main portion of the tip electrode (i.e., the non-stem portion of the tip electrode). The tip electrode conductor extends along the lead and is electrically coupled to one of the terminals disposed along the proximal end of the lead.

Figure 8A:
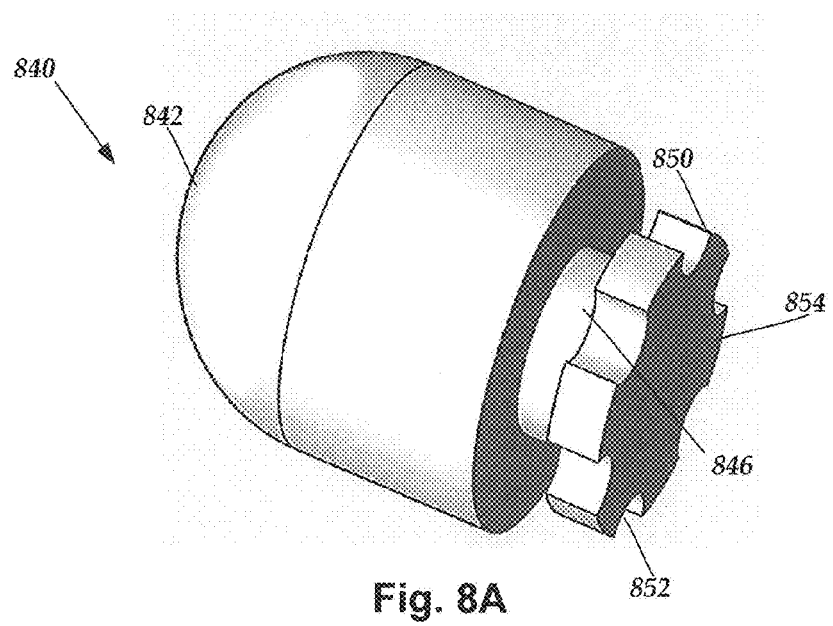
FIG. 8A is a schematic perspective view of one embodiment of a tip electrode with a stem and flange, according to the invention.

FIG. 8A illustrates another embodiment of a tip electrode 840 that includes an electrode body 842 and a stem 846 with a flange 850 attached to the end of the stem. The electrode body 842 includes at least a portion of the surface that is exposed to tissue, when the lead is implanted, for providing stimulation to the tissue. The flange may have any suitable shape including, but not limited to, disc-shaped, square-shaped, hexagonal-shaped, octagonal-shaped, triangular-shaped, and the like. In the illustrated embodiment, the flange is gear-shaped with a disc having regular indentations 852 formed in the sides of the disc leaving regular protrusions 854 around the edge of the disc. The tip electrode conductor (not shown) can be attached to any portion of the tip electrode including, but not limited to, the flange 850, the protrusions 854 of the flange, or the indentations 852 within the flange.

When the lead body is formed, the material of the lead body forms around the stem 846 and flange 850 of the tip electrode 840 which facilitates retention of the tip electrode within the lead body of the resulting lead. The flange 850 hinders extraction of the tip electrode 840 from the lead body. Portions of the lead body formed within the indentations 852 and around the protrusions 854 of the flange may facilitate both retention of the tip electrode on the lead and reduce the likelihood of rotation of the tip electrode. Typically, a non-circular flange will provide some resistance to rotation of the tip electrode.

Figure 8B:
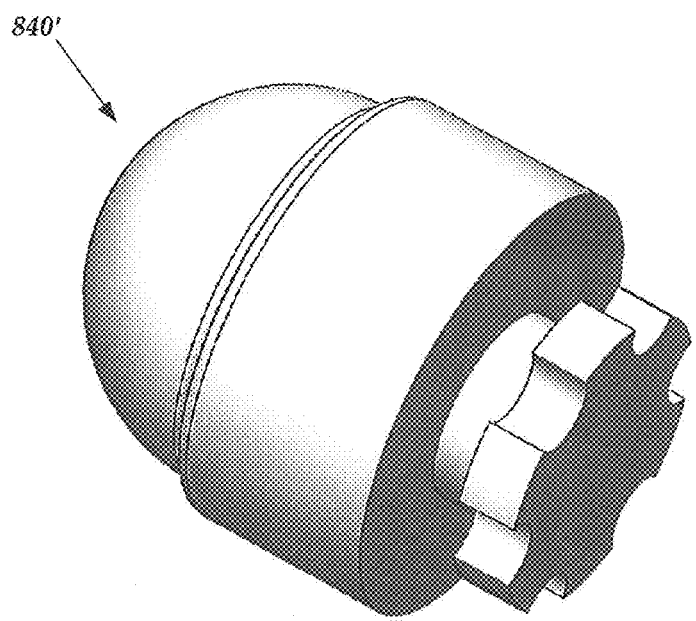
FIG. 8B is a schematic perspective view of one embodiment of a pre-electrode that can be ground down to form the tip electrode of FIG. 8A, according to the invention.

In at least some embodiments, a pre-electrode 840', as illustrated in FIG. 8B, is provided during manufacture. The lead body is formed around this pre-electrode 840'. Then the lead body and pre-electrode 840' are ground down to obtain the tip electrode 840 of FIG. 8A. This grinding process also removes excess lead body material leaving the lead body at the desired diameter.

Figure 9A:
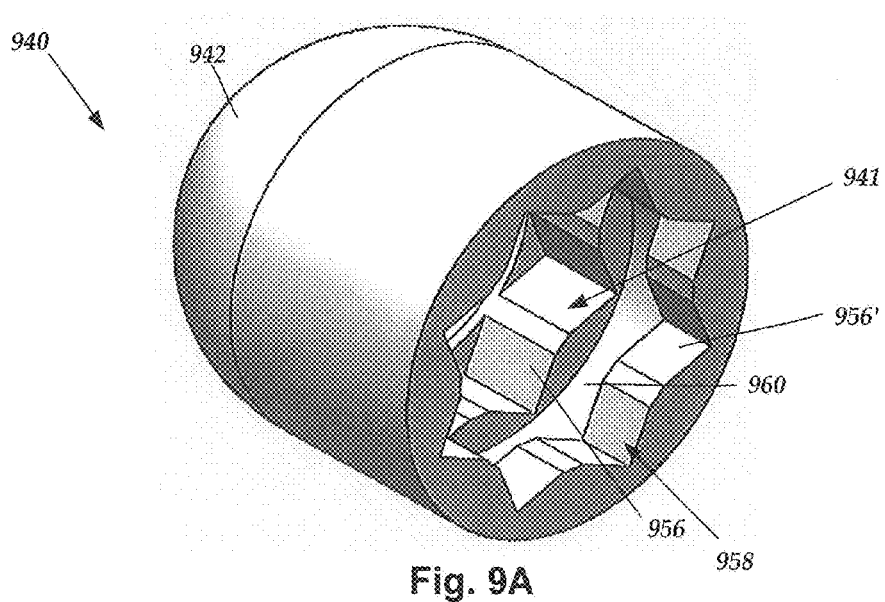
FIG. 9A is a schematic perspective view of one embodiment of a tip electrode with a shaped interior lumen, according to the invention.

FIG. 9A illustrates an embodiment of a tip electrode 940 with an electrode body 942 and an interior lumen 941. The electrode body 942 includes at least a portion of the surface that is exposed to tissue, when the lead is implanted, for providing stimulation to the tissue. When the lead body is formed, the material of the lead body flows into the interior lumen 941 to facilitate retention of the tip electrode on the lead body of the resulting lead. The tip electrode 940 defines protrusions 956 on the surface that defines the interior lumen 941. These protrusions 956 facilitate retaining the tip electrode on the lead body and also resist rotation of the tip electrode around the lead body. In the illustrated embodiment, the pattern of protrusions 956 form a star shape in cross-section, but it will be recognized that outer regular and irregular shapes generated by protrusions into the interior lumen can be used to resist rotation of the tip electrode around the lead body.

In addition, the proximal end of the tip electrode 940 defines a non-circular opening 958 with protrusions 956' that form a flange with respect to an adjacent portion 960 of the interior surface of tip electrode 940 defining the interior lumen 941. These protrusions 956', and the resulting flange-like arrangement, resist rotation of the tip electrode around the lead body and also resist removal of the tip electrode from the distal end of the lead.

Figure 9B:
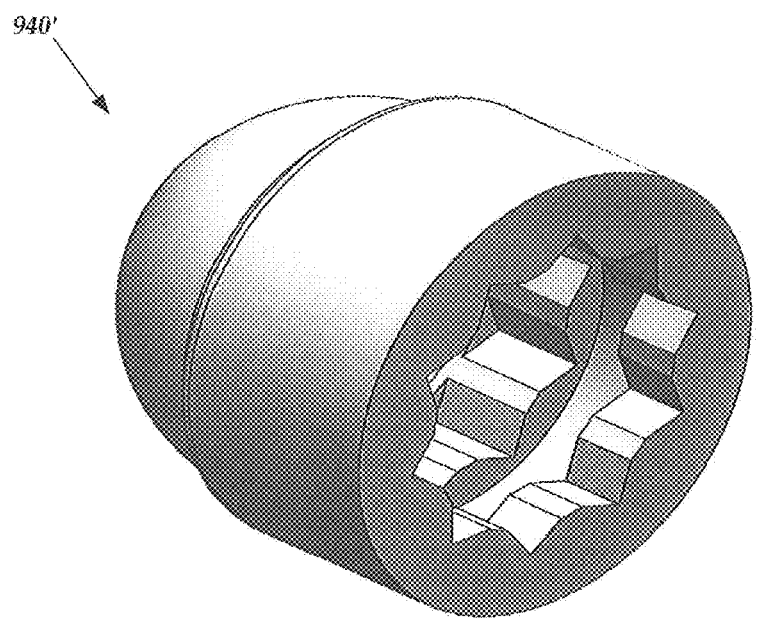
FIG. 9B is a schematic perspective view of one embodiment of a pre-electrode that can be ground down to form the tip electrode of FIG. 9A, according to the invention.

A tip electrode conductor (not shown) can be attached to any portion of the tip electrode including, but not limited to, the proximal end of the tip electrode, the protrusions 956', or the surface defining the interior lumen 941. In at least some embodiments, a pre-electrode 940', as illustrated in FIG. 9B, is provided during manufacture. The lead body is formed around, and within, this pre-electrode 940'. Then the lead body and pre-electrode 940' are ground down to obtain the tip electrode 940 of FIG. 9A. This grinding process also removes excess lead body material leaving the lead body at the desired diameter. It will be understood that this embodiment can be modified to include a base with the interior lumen and a separate plug as illustrated in FIGS. 5-6B.

Figure 10A:
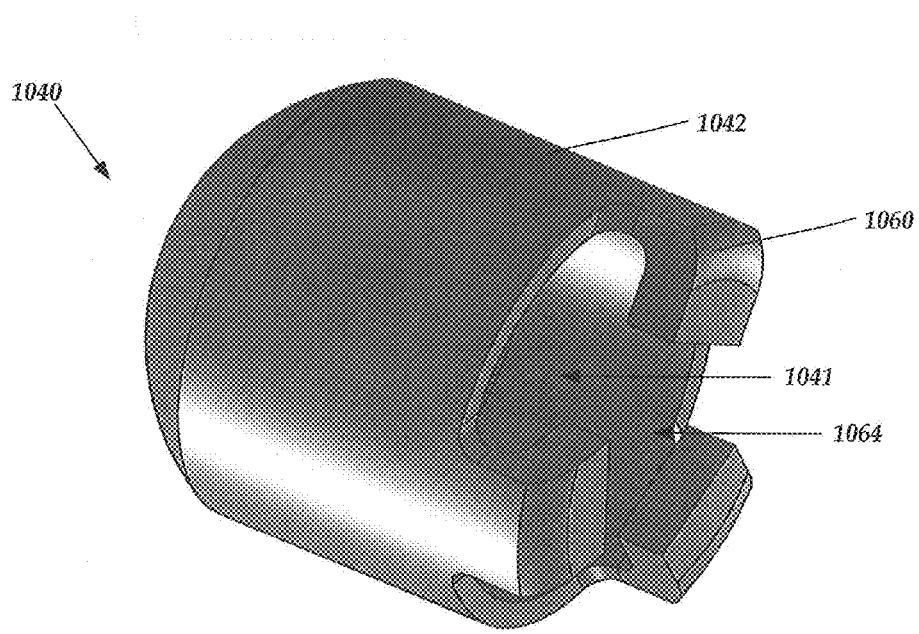
FIG. 10A is a schematic perspective view of one embodiment of a tip electrode with an interior lumen and multiple arms extending from an edge of the electrode over the opening of the interior lumen, according to the invention.

FIG. 10A illustrates an embodiment of a tip electrode 1040 with an electrode body 1042, an interior lumen 1041, and multiple arms 1060 extending from the electrode body 1042 and over the entrance 1064 to the interior lumen 1041. The electrode body 1042 includes at least a portion of the surface that is exposed to tissue, when the lead is implanted, for providing stimulation to the tissue. When the lead body is formed, the material of the lead body flows into the interior lumen 941 to facilitates retention of the tip electrode within the lead body of the resulting lead. These arms 1060 facilitate retaining the tip electrode on the lead body and also resist rotation of the tip electrode around the lead body. In the illustrated embodiment, tip electrode 1040 has three arms 1060, but it will be recognized that any number of arms can be used including, but not limited to, one, two, thee, four, six, or more arms. The arms 1060 can be distributed around the edge of the electrode body 1042 in any regular or irregular arrangement.

Figure 10B:
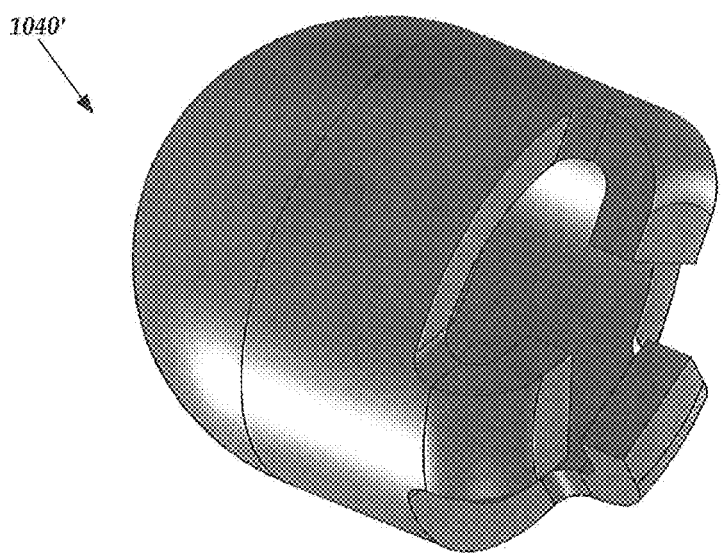
FIG. 10B is a schematic perspective view of one embodiment of a pre-electrode that can be ground down to form the tip electrode of FIG. 10A, according to the invention.

The tip electrode conductor (not shown) can be attached to any portion of the tip electrode including, but not limited to, the proximal end of the tip electrode, the arms 1060, or the surface defining the interior lumen 1041. In at least some embodiments, a pre-electrode 1040', as illustrated in FIG. 10B, is provided during manufacture. The lead body is formed around, and within, this pre-electrode 1040'. Then the lead body and pre-electrode 1040' are ground down to obtain the tip electrode 1040 of FIG. 10A. This grinding process also removes excess lead body material leaving the lead body at the desired diameter. It will be understood that this embodiment can be modified to include a base with the interior lumen and arms and a separate plug as illustrated in FIGS. 5-6B.

The above specification, examples, and data provide a description of the manufacture and use of the composition of the invention. Since many embodiments of the invention can be made without departing from the spirit and scope of the invention, the invention also resides in the claims hereinafter appended.

The invention claimed is:

1. An implantable electrical stimulation lead, comprising:
   a lead body comprising a distal portion, a distal tip, and a proximal portion; and
   a plurality of electrodes disposed along the distal portion of the lead body, the plurality of electrodes comprising a tip electrode disposed on the distal tip of the lead body, the tip electrode having a conductive base and a separate conductive plug attached to the base, wherein a portion of the base and the plug are exposed on an exterior of the lead and the base defines an interior lumen closed at one end by the plug, wherein a portion of the lead body extends into the interior lumen of the base;
   a plurality of terminals disposed along the proximal portion of the lead; and
   a plurality of conductors, each conductor electrically coupling at least one of the electrodes to at least one of the terminals.

2. The implantable electrical stimulation lead of claim 1, wherein the base is in electrical communication with the plug.

3. The implantable electrical stimulation lead of claim 1, wherein the plurality of electrodes further comprises a plurality of segmented electrodes.

4. The implantable electrical stimulation lead of claim 3, wherein the plurality of electrodes further comprises at least one ring electrode.

5. An implantable electrical stimulation lead, comprising:
   a lead body comprising a distal portion, a distal tip, and a proximal portion;
   a plurality of electrodes disposed along the distal portion of the lead body, the plurality of electrodes comprising a tip electrode disposed on the distal tip of the lead body, the tip electrode having an electrode body, a stem extending from the electrode body, and a plurality of shaped retention features extending from the stem, wherein a portion of the lead body extends around the stein and shaped retention features, wherein the shaped retention features facilitate retention of the tip electrode on the lead body;
   a plurality of terminals disposed along the proximal portion of the lead; and
   a plurality of conductors, each conductor electrically coupling at least one of the electrodes to at least one of the terminals.

6. The implantable electrical stimulation lead of claim 5, wherein the plurality of shaped retention features comprises at least one shaped retention feature having a sloped edge on one side and a stepped edge on an opposite side.

7. The implantable electrical stimulation lead of claim 5, wherein the plurality of shaped retention features comprises at least one protruding thread.

8. The implantable electrical stimulation lead of claim 5, wherein the plurality of shaped retention features comprises at least one stepped feature.

9. An implantable electrical stimulation lead, comprising:
   a lead body comprising a distal portion, a distal tip, and a proximal portion;
   a plurality of electrodes disposed along the distal portion of the lead body, the plurality of electrodes comprising a tip electrode disposed on the distal tip of the lead body, the tip electrode having an electrode body, a stem extending from the electrode body, and a flange attached to the stem opposite the electrode body, wherein a portion of the lead body extends around and over the stem and flange, wherein the flange facilitates retention of the tip electrode on the lead body;

a plurality of terminals disposed along the proximal portion of the lead; and a plurality of conductors, each conductor electrically coupling at least one of the electrodes to at least one of the terminals.

10. The implantable electrical stimulation lead of claim 9, wherein the flange is non-circular and resists rotation of the tip electrode around the distal tip of the lead body.

11. The implantable electrical stimulation lead of claim 10, wherein the flange comprises a plurality of indentations.

12. The implantable electrical stimulation lead of claim 11, wherein the plurality of conductors comprises a tip electrode conductor coupled to the flange of the tip electrode at one of the plurality of indentations.

13. An implantable electrical stimulation lead, comprising:

a lead body comprising a distal portion, a distal tip, and a proximal portion;

a plurality of electrodes disposed along the distal portion of the lead body, the plurality of electrodes comprising a tip electrode disposed on the distal tip of the lead body, the tip electrode having an electrode body, wherein the electrode body defines an interior lumen and a plurality of protrusions extending into the interior lumen, wherein a portion of the lead body extends into the interior lumen of the electrode body and wherein the plurality of protrusions in the interior lumen facilitates retention of the tip electrode on the lead body and hinders rotation of the tip electrode around the distal tip of the lead body;

a plurality of terminals disposed along the proximal portion of the lead; and a plurality of conductors, each conductor electrically coupling at least one of the electrodes to at least one of the terminals.

14. The implantable electrical stimulation lead of claim 13, wherein the electrode body further defines an opening to the interior lumen with a plurality of protrusions formed around the opening to give the opening a non-circular shape.

15. The implantable electrical stimulation lead of claim 14, wherein the plurality of protrusions formed around the opening provide a flange-like arrangement with respect to an adjacent surface of the interior lumen.

16. The implantable electrical stimulation lead of claim 13, wherein the electrode body further comprises a base and a separate plug attached to the base.

17. An implantable electrical stimulation lead, comprising:

a lead body comprising a distal portion, a distal tip, and a proximal portion;

a plurality of electrodes disposed along the distal portion of the lead body, the plurality of electrodes comprising a tip electrode disposed on the distal tip of the lead body, the tip electrode having an electrode body and a plurality of arms extending from the electrode body, wherein the electrode body defines an interior lumen and an opening to the interior lumen and wherein the plurality of arms extends over the opening to the interior lumen, wherein a portion of the lead body extends into the interior lumen of the electrode body and around the plurality of arms, wherein the plurality of arms facilitates retention of the tip electrode on the lead body;

a plurality of terminals disposed along the proximal portion of the lead; and a plurality of conductors, each conductor electrically coupling at least one of the electrodes to at least one of the terminals.

18. The implantable electrical stimulation lead of claim 17, wherein the arms are placed at regular intervals around the electrode body.

19. The implantable electrical stimulation lead of claim 17, wherein the plurality of electrodes further comprises a plurality of segmented electrodes.

20. The implantable electrical stimulation lead of claim 17, wherein the electrode body further comprises a base and a separate plug attached to the base.

* * * * *